United States Patent [19]

Cardinaux et al.

[11] 4,405,607
[45] Sep. 20, 1983

[54] NOVEL PENTAPEPTIDES, PROCESSES FOR THEIR PRODUCTION, PHARMACEUTICAL COMPOSITIONS COMPRISING SAID PENTAPEPTIDES AND THEIR USE

[75] Inventors: François Cardinaux; René Huguenin, both of Reinach; Janos Pless, Basel, all of Switzerland

[73] Assignee: Sandoz Ltd., Basel, Switzerland

[21] Appl. No.: 282,045

[22] Filed: Jul. 10, 1981

[30] Foreign Application Priority Data

Jul. 17, 1980 [CH] Switzerland ..................... 5483/80
Nov. 26, 1980 [CH] Switzerland ..................... 8752/80

[51] Int. Cl.³ ..................... A61K 37/00; C07C 103/52
[52] U.S. Cl. ..................... 424/177; 260/112.5 E
[58] Field of Search ............ 260/112.5 E; 424/177

[56] References Cited

U.S. PATENT DOCUMENTS

| | | | |
|---|---|---|---|
| 4,254,023 | 3/1981 | Stewart et al. | 260/112.5 E |
| 4,261,888 | 4/1981 | Bauer et al. | 260/112.5 E |
| 4,283,329 | 8/1981 | Gesellchen et al. | 260/112.5 E |
| 4,322,339 | 3/1982 | Gesellchen et al. | 260/112.5 E |

OTHER PUBLICATIONS

Biol. Abstr. 70, 66983.

Primary Examiner—Delbert R. Phillips

Attorney, Agent, or Firm—Gerald D. Sharkin; Robert S. Honor; Thomas O. McGovern

[57] ABSTRACT

Pentapeptides of formula I,

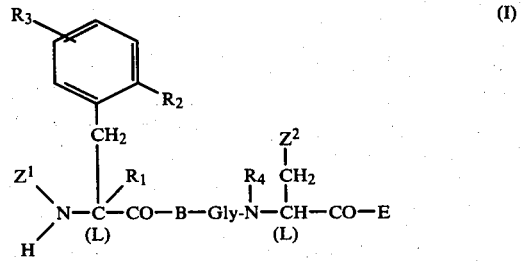

wherein $Z^1$=H, $CH_3$ or amidino; $R_1$=H or alkyl and $R_2$=H or $R_1+R_2$=—$CH_2$—$CH_2$—; $R_3$=m- or p—OH or -alkoxy; B=residue of a (D)-α-amino acid; $R_4$=H or alkyl; $Z^2$=optionally substituted phenyl; and E=β-amino alcohol residue (whereby when $Z^1$=H or $CH_3$, $R_4$=$C_{3-4}$-alkyl) as well as their esters and the acid addition salts and complexes of such peptides and esters. Compounds according to the invention have valuable pharmacological, in particular LH-secretion inhibiting activity.

15 Claims, No Drawings

NOVEL PENTAPEPTIDES, PROCESSES FOR THEIR PRODUCTION, PHARMACEUTICAL COMPOSITIONS COMPRISING SAID PENTAPEPTIDES AND THEIR USE

The present invention relates to pentapeptides of formula I,

wherein
A is a residue of formula

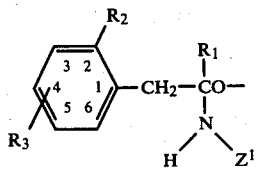

wherein
$Z^1$ is hydrogen, methyl or amidino,
$R_1$ is hydrogen or $C_{1-4}$-alkyl and $R_2$ is hydrogen or $R_1$ and $R_2$ together represent an ethylene bridge and
$R_3$ is hydroxy or $C_{1-4}$-alkoxy in the 3-, 4- or or 5-position;
B is the residue of an α-amino acid;
D is a residue of formula

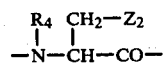

wherein
$R_4$ is hydrogen or $C_{1-4}$-alkyl and
$Z^2$ is optionally substituted phenyl; and
E is the residue of a β-amino alcohol attached to the adjacent carbonyl group via the β-N atom; whereby the residues A and D have the (L)-configuration, the residue E has the (D)- or (L)-configuration and the residue B has the (D)-configuration; with the proviso that when $Z^1$ is hydrogen or methyl, $R_4$ is $C_{3-4}$-alkyl; as well as the physiologically hydrolysable, physiologically acceptable esters thereof and the salts and complexes of such pentapeptides and esters. In describing the polypeptides of the invention as pentapeptides it will be noted that the aminoalcohol group E is regarded as an aminoacid derivative, By "amidino" is meant the group of formula

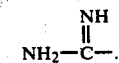

When $Z^1$ is amidino, $R_4$ is hydrogen or $C_{1-4}$-alkyl. When $Z^1$ is hydrogen or methyl, $R_4$ is $C_{3-4}$-alkyl.

Compounds according to the present invention wherein, in formula I, $Z^1$ is hydrogen or methyl, belong to the class of compounds disclosed in DOS No. 27 02 711 and equivalent U.K. patent specification No. 1,578,873. All compounds according to the present invention are novel.

As hereinafter described, they possess advantageous biological properties in particular luteinising hormone secretion inhibiting activity and are useful as pharmaceutically active substances.

$Z^2$ may be unsubstituted phenyl or substituted phenyl, i.e. phenyl bearing one or more, appropriate substituents, as known in the art.

By "the residue of a β-amino alcohol" is meant the residue corresponding to that of an α-amino acid in which the carboxyl group is replaced by —CH$_2$OH. The residue E may have either the (L)- or the (D)-configuration. Throughout the present specification and claims by an "(L)-β-amino alcohol residue" and a "(D)-β-amino alcohol residue" are meant those residues wherein the relative configuration is that of the corresponding (L)-α-amino acid and (D)-α-amino acid residues respectively [the carboxyl group of said (L)- or (D)-amino acid residue being replaced in each case by —CH$_2$OH]. It is to be understood that such residues may bear a $C_{1-4}$-alkyl substituent at the β-N-atom.

In the pentapeptides of formula I, the following significances or combinations thereof are preferred:
1. $R_1$ and $R_2$ are both hydrogen.
2. $R_3$ is hydroxy. Most preferably $R_3$ is in the 4-position and is especially 4-hydroxy.
3. B is the residue of the (D)-isomer of a naturally occurring α-amino acid in particular a naturally occurring non-aromatic α-amino acid. Most preferably B is -(D)-Ala-.
4. $R_4$ is $C_{1-4}$-alkyl, e.g. methyl. When $R_4$ is $C_{3-4}$-alkyl (both in the case when $Z^1$ is hydrogen or methyl and when $Z^1$ is amidino) this is preferably n-propyl, i-propyl or n-butyl, especially n-propyl.
5. $Z_2$ is phenyl or phenyl mono- or di-substituted by halogen, nitro, $C_{1-4}$-alkyl (especially methyl) and $C_{1-4}$-alkoxy (especially methoxy). (By "halogen", as used throughout the present specification and claims, is meant fluorine, chlorine and bromine).

More preferably $Z_2$ is phenyl or phenyl mono- or disubstituted by one or two members selected from the group consisting of fluorine, chlorine and nitro, especially fluorine. When $Z_2$ is substituted phenyl, this is preferably mono-substituted phenyl particularly, m- or p-substituted phenyl. Most preferably $Z^2$ is phenyl or m- or p-fluorophenyl, especially phenyl or p-fluorophenyl.

6. E is a group of formula

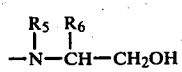

wherein
$R_5$ is hydrogen or $C_{1-4}$-alkyl and
$R_6$ is hydrogen, the substituent attaching to the α-carbon atom of a natural α-amino acid, a group of formula

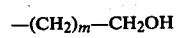

wherein m is an integer of from 1 to 6, or a group of formula

wherein $R_7$ is $C_{1-5}$-alkyl and n and p, each independently of the other, are zero, 1 or 2, with the proviso that, when n is 1 and p is zero, $R_7$ is other than methyl.
6.1. $R_5$ is preferably hydrogen.
6.2. As the substituent attaching to the α-carbon atom of a natural α-amino acid, $R_6$ is preferably a group of formula CH$_3$—S—CH$_2$—CH$_2$—, HO—CH$_2$—, CH$_3$—CH(OH)— or H$_2$NCO—CH$_2$—CH$_2$—.

6.3. When $R_6$ has a meaning other than under 6.2., it is preferably a group of formula $CH_3$—SO—$CH_2$—$CH_2$— or $CH_3$—$SO_2$—$CH_2$—$CH_2$—.

6.4. Most preferably $R_6$ is the group of formula $CH_3$—SO—$CH_2$—$CH_2$—.

6.5. The residue E, including preferred residues E defined under 6. and 6.1. through 6.4. above, preferably has the (L)-configuration (as hereinbefore defined). Most preferably E is -Met(O)-ol, i.e. the residue of (L)-methioninol sulfoxide.

Hydroxy groups in the pentapeptides of formula I, in particular the hydroxy group of the terminal $\beta$-amino alcohol residue E, may be esterified to form corresponding physiologically hydrolysable, physiologically acceptable esters, i.e. esters which hydrolyse to yield a physiologically acceptable acid.

Suitable ester forms include e.g. the esters formed with mono- and di-carboxylic acids, in particular the esters with $C_2$-$C_5$-carboxylic acids such as the acetates as well as aromatic carboxylic acids such as the benzoates.

The pentapeptides of formula I and their esters may exist in acid addition salt form or in the form of complexes. Acid addition salts may be formed with e.g. organic acids, polymeric acids and inorganic acids. Such acid addition salt forms include e.g. the hydrochlorides and acetates. By complexes are to be understood compounds of known type, formed from pentapeptides of formula I and their esters on addition of inorganic substances, e.g. inorganic salts or hydroxides such as Ca-, Mg-, Al-, Co- and especially Zn-salts, or on addition of polymeric organic substances.

One group of compounds according to the present invention comprises the pentapeptides of formula I, wherein $Z^1$ is amidino, B is -(D)-Ala-, $Z^2$ is phenyl or phenyl mono- or di-substituted by halogen, nitro, $C_{1-4}$-alkyl or $C_{1-4}$-alkoxy and $R_1$, $R_2$, $R_3$, $R_4$ and E have the meanings given for formula I, as well as the acid addition salts and complexes thereof.

A second group of compounds according to the present invention comprises the pentapeptides of formula I, wherein $Z^1$ is hydrogen or methyl, $R_1$ and $R_2$ are both hydrogen or together represent an ethylene bridge, $R_3$ is hydroxy in the 4-position, B is -(D)-Ala-, $R_4$ is $C_{3-4}$-alkyl (especially n-propyl, n-butyl and i-butyl), $Z^2$ is phenyl or phenyl mono- or di-substituted by one or two substituents selected from the group consisting of halogen, nitro, $C_{1-4}$-alkyl or $C_{1-4}$-alkoxy and E is -Met(O)-ol, as well as the acid addition salts and complexes thereof.

The present invention also provides a process for the production of the compounds according to the invention. These compounds may be prepared by methods known in the art of peptide chemistry or by an obvious chemical equivalent thereof, for example by a process comprising:

(a) removing at least one protecting group from a pentapeptide or ester thereof in protected form and having the sequence indicated in formula I:

(b) linking together by an amide bond two peptide units each of which contains at least one amino acid or amino alcohol residue in protected or unprotected form, the peptide units being such that a pentapeptide or ester thereof in protected or unprotected form and having the sequence indicated in formula I is obtained and, when required, carrying out process step (a);

(c) oxidising a pentapeptide or ester thereof in protected or unprotected form and having the sequence indicated in formula I in which the residue E is a methioninol residue, so as to obtain the corresponding pentapeptide or ester in which E is a methioninol-sulfoxide or -sulfone residue and, when required, carrying out process step (a);

(d) reacting a pentapeptide or ester thereof in protected or unprotected form and having the sequence indicated in formula I in which $Z^1$ is hydrogen with a reagent capable of introducing an amidino group $Z^1$ at the N-terminal of said pentapeptide or ester and, when required, carrying out process step (a);

(e) esterifying a pentapeptide in protected or unprotected form and having the sequence indicated in formula I in which at least one free hydroxy group is present and, when required carrying out process step (a); and recovering the obtained pentapeptide or ester thereof in free form or in acid addition salt or complex form.

The above processes may for example be carried out analogously to the processes described in the accompanying examples. Insofar as the production of the starting materials is not particularly described, the compounds are known or may be produced and purified in accordance with methods known in the art.

A suitable reagent for carrying out process step (d) is e.g. 1-amidino-3,5-dimethylpyrazole, conveniently employed in salt form, e.g. in the form of the nitrate.

The reaction is conveniently performed in a solvent or diluent which is inert under the conditions of reaction to the reaction components, for example dimethyl formamide.

The pentapeptides and esters of the invention as well as their physiologically acceptable acid addition salts and complexes exhibit valuable pharmacological properties as indicated in animal tests. In particular they exhibit luteinising hormone (LH) secretion inhibiting and CNS-depressant activity as indicated e.g. in the following test methods.

1. LH-secretion Inhibiting Activity

Adult female rats each weighing 200-250 mg and having a proven, regular 4-day oestrus cycle are maintained under standard conditions [14 hrs. light (04.00–18.00), 24° C. and 55–60% relative humidity] and allowed access ad libitum to food and water. The test-compound is administered s.c. during the pro-oestrus phase, the doses being administered once at 13.00h and again at 16.00h. 20 hrs. after the first dose the rats are sacrificed, the fallopian tubes exposed and the total number of ova in both tubes counted with a dissecting microscope. Evaluation is carried out on the "all-or-nothing" principle, ovulation being considered as inhibited only when no ova are found. Five rats are used per dose. Compounds according to the invention are active in this test when administered at a dosage of $2 \times 0.01$ to 0.3 mg/kg body weight s.c.

2. CNS-depressant Activity

Observation of changes in the spontaneous behaviour of mice and rats (P.O.T.-test) in accordance with the principles described by J. H. Nodide et al. in "Animal and Clinical Pharmacological Techniques in Drug Evaluation", Chicago, 1964 and in "Psychopharmacologia", 13, 222–257 (Berlin, 1968). Compounds according to the invention are active in this test when administered at a dosage of from 0.001 to 1.0 mg/kg body weight s.c.

The said pentapeptides, esters, salts and complexes are accordingly useful (i) in the treatment of subjects with disorders having an aetiology associated with or modulated by LH-secretion or having an aetiology in which the physiological regulation of LH-secretion is implicated e.g. in the treatment of prostate hypertrophy or in the treatment of menopausal syndrome, in particular post-menopausal hot-flashes, e.g. in accordance with the studies reported by Tataryn et al. ["Thermoregulatory mechanisms and their Therapeutic Implications, 4th. Int. Symp. on the Pharmacology of Thermoregulation, Oxford, 1979" published—Karger, Basel 1980, pp 202–207] and Casper et al. ["Science", 205, pp 823–825 (1979)] and (ii) as psychopharmaceutica e.g. in the treatment of psychotic conditions.

The amount of compound administered will of course vary according to e.g. the particular compound employed, the mode of administration, the condition to be treated and the therapy desired. In general for both uses (i) and (ii) above satisfactory results are obtained when administered at a daily dosage of from 0.001 to 1 mg/kg body weight, conveniently given in divided doses 2 to 4 times a day or in sustained release form. For larger mammals the total daily dosage for oral administration is in the range of from about 0.1 to about 10 mg pentapeptide or ester and suitable unit dosage forms, contain from about 0.025 to 5.0 mg of a pentapeptide or ester as aforesaid or of an equivalent amount of a pharmaceutically acceptable salt or complex thereof, together with a solid or liquid pharmaceutical diluent or carrier therefor.

In accordance with the foregoing the present invention further provides:

(i) a method of inhibiting LH-secretion, in particular of treating prostatic hypertrophy or menopausal syndrome, especially post-menopausal hot flashes as well as a method of treating psychotic disturbance in a subject in need of such treatment, which method comprises administering to said subject an effective amount of a pentapeptide of formula I or a physiologically hydrolysable, physiologically acceptable ester thereof or of a physiologically acceptable acid addition salt or complex of such pentapeptide or ester, as well as (ii) pentapeptides, esters, acid addition salts and complexes as recited under (i) above as pharmaceuticals, i.e. for use in the treatment of the human or animal body by therapy, in particular for use in a method as defined under (i) above, and (iii) pharmaceutical compositions comprising a pentapeptide, ester, acid addition salt or complex as recited under (i) above as active ingredient.

Throughout the present description and claims and in the accompanying examples, the following abbreviations are used:

Met-ol = the (L)-methioninol residue of formula $CH_3SCH_2CH_2CH(CH_2OH)NH—$
Met(O)-ol = the (L)-methioninolsulfoxide residue of formula $CH_3—S(O)—CH_2CH_2CH(CH_2OH)—NH—$
MeTyr = —N-methyl-Tyr—
MeTyr(Bu$^t$) = N-methyl-O-t.butyl-Tyr—
MePhe = —N-methyl-Phe—
(N-propyl)Phe = —N-n-propyl-Phe—
(N-i.butyl)Phe = —N-i.butyl-Phe—
(N-butyl)Phe = —N-n-butyl-Phe—
(N-propyl)Phe(p-F) = —N-n-propyl-p-fluoro-Phe—
DMF = dimethylformamide
Boc = t.butyloxycarbonyl
Z = benzyloxycarbonyl In accordance with standard nomenclature all amino acid residues indicated by the three-letter abbreviation are understood as being in the L-configuration unless otherwise indicated.

EXAMPLE 1

H-MeTyr-(D)-Ala-Gly-(N-propyl)Phe-Met(O)-ol trifluoroacetate 2.7 g Boc-MeTyr(Bu$^t$)-(D)-Ala-Gly-(N-propyl)Phe-Met(O)-ol are dissolved at 20° C. in a mixture of 5 ml trifluoroacetic acid and 5 ml methylene chloride. After 30 minutes, ethyl ether is added and the obtained precipitate filtered, washed with ether and dried. The raw-product is purified by counter-current partitioning using a chloroform:methanol:water mixture [65:35:10(v/v)] followed by chromatography on silica gel using a mixture of chloroform:methanol:water:acetic acid [70:20:3:3(v/v)] as eluant. The title compound is obtained after recrystallisation from methanol/ethyl acetate: $[\alpha]_D^{20} = -19.3°$ (c=1 in 95% acetic acid).

The starting material for use in the above process is obtained as follows:

(a) H-Phe-Met-ol hydrochloride

A solution of 21.1 g Boc-Phe-Met-ol in 20 ml dioxane is added at 0° C. to 130 ml 5 N HCl in dioxane. After reaction for 1 hour at 0° C., 400 ml ethyl ester are added, the precipitate filtered under suction, washed with ethyl ether and dried over $P_2O_5$ and KOH under vacuum, to yield the title compound: $[\alpha]_D^{20} = +8.8°$ (c=1 in DMF), decomposition at 200° C.

(b) H-(N-propyl)Phe-Met-ol 6.3 g NaBH$_3$CN, followed after 5 minutes by 2.0 ml propionaldehyde, are added at 20° C. to a solution of 8.0 g H-Phe-Met-ol hydrochloride in 100 ml methanol. After reaction for 2.5 hours the solvent is completely evaporated under vacuum, 50 ml water are added and the pH rendered strongly basic (pH≃12) by the addition of 10 N NaOH, whereupon a brown precipitate is formed. The precipitate is filtered under suction, washed thoroughly with water and the still damp product re-crystallised from ethanol/water with the addition of active-charcoal to yield the title compound: $[\alpha]_D^{20} = -30.6°$ [c=1 in DMF], decomposition at 130° C.

(c) Boc-Gly-(N-propyl)Phe-Met-ol 2.2 ml pivaloyl chloride, followed by 3.0 ml N-ethyl-diisopropylamine are added at −20° C. to a solution of 3.1 g Boc-Gly-OH in 20 ml tetrahydrofuran and the obtained mixture stirred for 15 minutes at −15° C. A solution of 5.7 g H-(N-propyl)Phe-Met-ol in 30 ml tetrahydrofuran and 10 ml DMF is then added and the whole stirred for 1 hour at −15° C., 1 hour at 0° C. and 20 hours at 10° C. 20 ml 1 N KHCO$_3$ are added, extraction effected with ethyl acetate, washed with dilute KHCO$_3$-/KHSO$_4$-solution and water, dried and the solvent evaporated under vacuum. The raw product is purified chromatographically on silica gel using methylene chloride/methanol as eluant.

(d) H-Gly-(N-propyl)Phe-Met-ol trifluoroacetate 3.1 g Boc-Gly-(N-propyl)Phe-Met-ol are dissolved in a mixture comprising 5 ml trifluoroacetic acid and 5 ml methylene chloride. After 30 minutes the solution is evaporated under vacuum at 20° C., 20 ml dioxane are added, evaporation repeated and the residue dried over P₂O₅ and KOH under vacuum. The amorphorus product is used directly in the next step.

(e)
Boc-MeTyr(Bu$^t$)-(D)-Ala-Gly-(N-propyl)Phe-Met-ol 1.7 g 1-hydroxybenzotriazole are added to a solution of 2.7 g Boc-MeTyr(Bu$^t$)-(D)-Ala-OH in 20 ml DMF, followed by 1.45 g N,N'-dicyclohexylcarbodiimide, the latter being added at 0° C. After 1 hour at 0° C. and 1 hour at 20° C. the precipitated dicyclohexyl urea is filtered off and a solution of 4 g H-Gly-(N-propyl)Phe-Met-ol trifluoroacetate in 10 ml DMF and 2 ml N-methyl-morpholine is added to the filtrate. The reaction mixture is allowed to stand for 15 hours at 20° C., filtered and the filtrate thoroughly concentrated under vacuum, taken up in ethyl acetate, washed with dilute KHCO₃- and KHSO₄-solution and with water, dried and the solvent evaporated under vacuum.

(f)
Boc-MeTyr(Bu$^t$)-(D)-Ala-Gly-(N-propyl)Phe-Met(O)-ol 0.34 ml 11 M H₂O₂ are added to a solution of 2.7 g Boc-MeTyr(Bu$^t$)-(D)-Ala-Gly-(N-propyl)Phe-Met-ol in 15 ml acetic acid. Precipitation is effected after 10 minutes, using ether:hexane (1:1), the precipitate filtered, washed thoroughly with hexane and dried. The product is used directly for further reaction as hereinabove described.

EXAMPLE 2

The following compounds are prepared analogously to example 1.

2.1. H-MeTyr-(D)-Ala-Gly-(N-i.butyl)Phe-Met(O)-ol trifluoroacetate: $[\alpha]_D^{20} = -13.7°$ (c=1 in 95% CH₃COOH).

2.2. H-MeTyr-(D)-Ala-Gly-(N-butyl)Phe-Met(O)-ol trifluoroacetate: $[\alpha]_D^{20} = -7.9°$ (c=1 in 95% CH₃COOH).

2.3. H-MeTyr-(D)-Ala-Gly-(N-propyl)Phe(p-F)-Met-(O)-ol trifluoroacetate: $[\alpha]_D^{20} = -9.0°$ (c=1 in 95% CH₃COOH).

EXAMPLE 3

N$^\alpha$Amidino-Tyr-(D)-Ala-Gly-MePhe-Met(O)-ol acetate 1 g H-Tyr-(D)-Ala-Gly-MePHe-Met(O)-ol hydrochloride dissolved in 10 ml dimethylformamide is reacted with 1.9 g 1-amidino-3,5-dimethylpyrazole nitrate in 0.5 ml N-methylmorpholine and 0.8 ml triethylamine. After 5 days the reaction mixture is adjusted to pH 5-6 by the addition of 1 N acetic acid and evaporated to dryness under vacuum. The residue is dissolved in water and the solution passed onto a chromatographic column containing 50 g of a weakly acidic ion-exchanger. After washing with 0.1% acetic acid the product is eluted with an acetic acid gradient of from 0.1% to 95%. Fractions containing the title compound are collected and lyophilised, yielding the title compound as a light, amorphous powder, decomposing at 140°: $[\alpha]_D^{20} = -50.8°$ [c=0.7 in dimethylformamide].

EXAMPLE 4

N$^\alpha$-Amidino-Tyr-(D)-Ala-Gly-MePhe(p-F)-Met(O)-ol hydrochloride

The title compound is obtained analogously to example 1 employing H-Tyr-(D)-Ala-Gly-MePhe(p-F)-Met-(O)-ol hydrochloride as starting material. $[\alpha]_D^{20} = -29.3°$ (c=1 in 95% acetic acid).

EXAMPLE 5

N$^\alpha$-Amidino-Tyr-(D)-Ala-Gly-(N-propyl)Phe-Met-ol hydrochloride 1.3 ml 8 N HCl in dioxane followed by 0.35 ml t.-butyl nitrite are added to a solution of 1.04 g N$^\alpha$-amidino-Tyr-(D)-Ala-NH-NH₂ hydrochloride in 20 ml DMF at a temperature of −18° C. After standing for 10 minutes at −18° C. the reaction mixture is neutralised with 2.3 ml N-ethyl-diisopropylamine and combined with a precooled solution comprising 1.5 g H-Gly-(N-propyl)Phe-Met-ol hydrochloride and 0.62 ml N-ethyl-diisopropylamine in 15 ml DMF. After reaction for 1 hour at −15° C. and for a further 3 hours at −10° C. the solvent is evaporated under vacuum and the residue taken up in water and washed several times with methylene chloride. The aqueous phase is evaporated to ca. 60 ml, adsorbed onto a polystyrene adsorption resin, washed with water and eluted with aqueous methanol. After evaporation to dryness and precipitation from methanol/ethyl ether, the title compound is obtained: $[\alpha]_D^{20} = -41.0°$ (c=1 in DMF), decomposition at 90° C.

The starting materials for use in the above process are obtained as follows:

(a) H-(N-propyl)Phe-NH-NH-Z hydrochloride 10.0 g NaBH₃CN and, after a further 5 minutes, 3,2 ml propionaldehyde are added to a solution of 14.0 g H-Phe-NH-NH-Z hydrochloride in 120 ml methanol at 20° C. After reaction for 2.5 hours the solvent is evaporated under vacuum, 50 ml water are added, the pH is rendered strongly basic (≃pH12) by the addition of 10 N NaOH and the product extracted with methylene chloride. The extract is thoroughly washed with water, dried over Na₂SO₄ and treated with an excess of HCl in ethyl ether. Crystallisation is completed by the addition of further ether to yield the title compound: $[\alpha]_D^{20} = +42.5°$ (c=1 in DMF).

(b) Boc-Gly-(N-propyl)Phe-NH-NH-Z 11.8 ml pivaloylchloride are added to a solution of 16.8 g Boc-Gly-OH in 100 ml tetrahydrofuran at −20° C. and the mixture is stirred for 15 minutes at −15° C. A solution of 12.5 g H-(N-propyl)Phe-NH-NH-Z and 5.5 ml N-ethyl-diisopropylamine in 50 ml tetrahydrofuran are then added and the reaction mixture stirred for 1 hour at −15° C., 1 hour at 0° C. and 20 hours at 10° C. After treatment with 150 ml, 1 N KHCO₃, the product is extracted with ethyl acetate, washed with dilute KHCO₃ and KHSO₄ and water, dried over Na₂SO₄ and the solvent evaporated under vacuum. The title compound is purified chromatographically, using silica gel and methylene chloride/methanol as eluant.

(c) Boc-Gly-(N-propyl)Phe-NH-NH₂

21.1 g Boc-Gly-(N-propyl)Phe-NH-NH-Z in 100 ml methanol are hydrogenated in the presence of a palladium catalyst for 1 hour at 2-3 bar H₂. The solvent is evaporated under vacuum and the amorphous residue dried over P₂O₅ and KOH under vacuum, to yield the title compound: $[\alpha]_D^{20} = -39.4°$ (c=1 in DMF).

(d) Boc-Gly-(N-propyl)Phe-Met-ol 8.6 ml 8 N HCl in dioxane followed by 2.1 ml t-butylnitrite are added with stirring to a solution of 7.8 g Boc-Gly-(N-propyl)Phe-NH-NH$_2$ in 50 ml DMF at $-18°$ C. After standing for 10 minutes at $-18°$ C., the mixture is neutralised by the addition of 12.0 ml N-ethyl-diisopropylamine and combined with a pre-cooled solution of 5.4 g methioninol [CH$_3$SCH$_2$CH$_2$CH(NH$_2$)CH$_2$OH] in 30 ml DMF. After reaction for 3 hours at $-10°$ C. the reaction mixture is diluted with ethyl acetate, washed with dilute KHCO$_3$ and KHSO$_4$ and water and dried over Na$_2$SO$_4$. The solvent is evaporated under vacuum and the product purified chromatographically using silica gel and methylene chloride/methanol as eluant to yield the title compound.

(e) H-Gly-(N-propyl)Phe-Met-ol hydrochloride

A solution of 9.9 g Boc-Gly-(N-propyl)Phe-Met-ol in 20 ml ethyl ether is treated with 100 ml 5 N HCl in ethyl ether at 0° C. After a further hour at 0° C. the solvent is evaporated under vacuum and the residue re-crystallised from ethyl acetate/methanol/ethyl ether to yield the title compound: $[\alpha]_D^{20} = -72.5°$ (c=1 in DMF). The product decomposes at 60° C.

(f) Boc-Tyr-(D)-Ala-NH-NH-Z 6.6 ml of isobutylchloroformate are added to a solution of 14.1 g Boc-Tyr-OH and 5.6 ml N-methylmorpholine in 100 ml tetrahydrofuran at $-20°$ C.

After a further 5 minutes at $-20°$ C., a solution comprising 13.7 g H-(D)-Ala-NH-NH-Z hydrochloride and 5.0 ml N-methylmorpholine in 50 ml DMF is added. After reaction for 2.5 hours at $-15°$ C., 100 ml 1 N KHCO$_3$ are added and the mixture diluted with ethyl acetate, washed with dilute KHCO$_3$ and KHSO$_4$ and water and dried over Na$_2$SO$_4$. The title compound is recovered by evaporation of the solvent under vacuum and re-crystallisation of the residue from ethyl acetate/hexane/ethyl ether.

(g) H-Tyr-(D)-Ala-NH-NH-Z hydrochloride 100 ml 5 N HCl in ethyl ether are added to a solution of 25.0 g Boc-Tyr-(D)-Ala-NH-NH-Z in 50 ml ethyl acetate at 0°. Crystallisation is completed after 1.5 hours by the addition of further ethyl ether and the title compound recovered by filtration: $[\alpha]_D^{20} = +32.8°$ (c=1 in DMF), decomposition at 200° C.

(h) N$^\alpha$-Amidino-Tyr-(D)-Ala-NH-NH-Z hydrochloride 12.1 g of 1-amidino-3,5-dimethylpyrazole nitrate are added to a solution of 8.8 g H-Tyr-(D)-Ala-NH-NH-Z hydrochloride and 2.8 ml triethylamine in 50 ml DMF. The mixture is stirred for 4 days at 50°-60° C. and 3.0 ml triethylamine are added. The solvent is removed by evaporation under vacuum, the residue taken up in water and extracted several times with methylene chloride. The aqueous phase is then concentrated to ca. 400 ml, adsorbed onto a polystyrene adsorption resin and the title compound eluted as the nitrate using methanol/water as eluant. The eluate is evaporated to dryness, dried again under vacuum, dissolved in ethyl acetate in the presence of a minor quantity of ethanol and the title compound recovered as the hydrochloride by the addition of ethyl ether and of excess 5 N HCl in ethyl acetate. $[\alpha]_D^{20} = +23.3°$ (c=1 in DMF), decomposition at 50° C.

(i) N$^\alpha$-Amidino-Tyr-(D)-Ala-NH-NH$_2$ hydrochloride 1.6 g N$^\alpha$-amidino-Tyr-(D)-Ala-NH-NH-Z hydrochloride in 20 ml methanol are hydrogenated in the presence of a palladium catalyst at 2-3 bar H$_2$. After 30 minutes the catalyst is filtered off, the solvent evaporated under vacuum and the residue re-crystallised from methanol/ethyl ether to yield the title compound: $[\alpha]_D^{20} = +13.2°$ (c=1 in DMF), decomposition at 80° C.

EXAMPLE 6

N$^\alpha$-Amidino-Tyr-(D)-Ala-Gly-(N-propyl)Phe-Met(O)-ol hydrochloride 1.05 g N$^\alpha$-Amidino-Tyr-(D)-Ala-Gly-(N-propyl)-Phe-Met-ol hydrochloride (c.f. example 5) are dissolved in 10 ml acetic acid and oxidised at 20° C. using 0.15 ml 11 M H$_2$O$_2$. After 10 minutes the product is precipitated with ethyl ether. The raw product is purified by counter-current partitioning in a mixture of chloroform:methanol:water [65:35:10 (v/v)]. The title compound is obtained following re-crystallisation from methanol/ethyl ether: $[\alpha]_D^{20} = -33.6°$ (c=1 in 95% acetic acid).

We claim:

1. A pentapeptide of formula I,

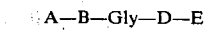

wherein A is a residue of formula

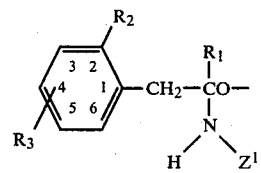

wherein

Z$^1$ is amidino,
R$_1$ is hydrogen or C$_{1-4}$ alkyl,
R$_2$ is hydrogen,
R$_3$ is hydroxy in the 4-position;
B is (D)-Ala
D is a residue of formula

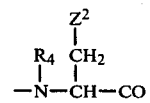

wherein
R$_4$ is hydrogen or C$_{1-4}$ alkyl and
Z$^2$ is phenyl or phenyl mono- or di-substituted by halogen, nitro, C$_{1-4}$ alkyl or C$_{1-4}$ alkoxy and
E is a group of the formula

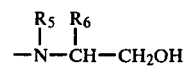

wherein
R$_5$ is hydrogen or C$_{1-4}$ alkyl and
R$_6$ is CH$_3$SCH$_2$CH$_2$—, HOCH$_2$—, CH$_3$—CH(OH)— or H$_2$NCOCH$_2$CH$_2$—, a group of formula $-(CH_2)_m-CH_2OH$ wherein m is an integer of from 1 to 6, or a group of formula $-(CH_2)_n-CH_2-S(O)_p-R_7$ wherein
$R_7$ is $C_{1-5}$ alkyl and n and p, each independently of the other, are zero, 1 or 2, with the proviso that, when n is 1 and p is zero, $R_7$ is other than methyl;
where the residues A and D have the (L)-configuration, and the residue E has the (D)- or (L)-configuration or a physiologically hydrolysable, physiologically acceptable ester thereof or a salt or complex of the pentapeptide or ester pharmaceutically acceptable.

2. $N^\alpha$-Amidino-Tyr-(D)-Ala-Gly-MePhe-Met(O)-ol.

3. $N^\alpha$-Amidino-Tyr-(D)-Ala-Gly-MePhe(p-F)-Met(O)-ol.

4. $N^\alpha$-Amidino-Tyr-(D)-Ala-Gly-(N-propyl)Phe-Met-ol.

5. $N^\alpha$-Amidino-Tyr-(D)-Ala-Gly-(N-propyl)Phe-Met(O)-ol.

6. A physiologically hydrolysable, physiologically acceptable ester of a pentapeptide as defined in any one of claims 2 to 5, or a pharmaceutically acceptable acid addition salt or complex of such a pentapeptide or ester.

7. A pharmaceutical composition useful in inhibiting luteinising hormone secretion or treating psychotic disturbances or pain comprising a pentapeptide or ester according to claim 1 or a pharmaceutically acceptable acid addition salt or complex thereof in an effective amount for inhibiting luteinising hormone or treating psychotic disturbances or pain, together with a pharmaceutically acceptable diluent or carrier therefor.

8. A method of inhibiting luteinising hormone secretion in a subject in need of such treatment, which method comprises administering to said subject an effective amount of a pentapeptide or ester according to claim 1 or a pharmaceutically acceptable acid addition salt or complex thereof.

9. A method according to claim 8 for the treatment of menopausal syndrome.

10. A method according to claim 9 for the treatment of post-menopausal hot flashes.

11. A method of treating psychotic disturbance or of treating pain in a subject in need of such treatment which method comprises administering to said subject an effective amount of a pentapeptide or ester according to claim 1 or a pharmaceutically acceptable acid addition salt or complex thereof.

12. A compound according to claim 1, in which $R_6$ is $CH_3-S-CH_2-CH_2-$, $HO-CH_2-$, $CH_3-CH(OH)-$ or $H_2NCO-CH_2CH_2-$.

13. A compound according to claim 1 in which $R_6$ is $CH_3-SO-CH_2-CH_2-$ or $CH_3-SO_2-CH_2-CH_2-$.

14. A compound according to claim 1 in which $R_6$ is $CH_3-SO-CH_2-CH_2-$.

15. A compound according to claim 1 in which A is TYR or H-MeTYR; $\beta$ is (D)-ALA, D is PHE or $(C_{1-4}alkyl)$Phe; and E is Met(O)-ol.

* * * * *